United States Patent [19]

Reinhardt et al.

[11] 4,400,540

[45] Aug. 23, 1983

[54] OXY AND THIOARYL-PHENYLATED AROMATIC BISCYCLOPENTADIENONES

[75] Inventors: Bruce A. Reinhardt, New Carlisle; Fred E. Arnold, Centerville, both of Ohio

[73] Assignee: The United States of America as represented by the Secretary of the Air Force, Washington, D.C.

[21] Appl. No.: 366,733

[22] Filed: Apr. 8, 1982

[51] Int. Cl.³ .............................................. C07C 49/792
[52] U.S. Cl. .................................... 568/31; 568/308; 562/488; 528/183

[58] Field of Search ................... 568/31, 312, 25, 306, 568/308; 528/183; 562/488

[56] References Cited

U.S. PATENT DOCUMENTS 4,108,835  8/1978  Arnold et al. ........................ 528/183
4,131,748  12/1978  Arnold et al. ........................ 562/488

Primary Examiner—Werren B. Lone
Attorney, Agent, or Firm—Donald J. Singer; Charles E. Bricker

[57] ABSTRACT

Oxy- and thio-aryl-phenylated aromatic biscyclopentadienones are prepared from aromatic bis-benzils and benzylketones.

3 Claims, No Drawings

OXY AND THIOARYL-PHENYLATED AROMATIC BISCYCLOPENTADIENONES

RIGHTS OF THE GOVERNMENT

The invention described herein may be manufactured and used by or for the Government of the United States for all governmental purposes without the payment of any royalty.

BACKGROUND OF THE INVENTION

This invention relates to aromatic biscyclopentadienones.

High temperature resins presently available have various drawbacks which limit their use in many applications. A serious one frequently encountered is the evolution of volatiles during the curing cycle, which makes it imperative that the entire curing cycle be carried out under pressure.

Acetylene-terminated compounds show promise for use in the preparation of matrix resins and adhesives for many high-temperature applications. These compounds can be polymerized thermally without the evolution of volatile by-products, thereby obviating the problem of void formation in composite structures and molded articles.

Although many of the aromatic, heterocyclic and aromatic heterocyclic polymers exhibit superior mechanical and thermal properties, many of these polymers also exhibit the disadvantage that they are soluble only in strong solvents, generally strong acids, which is a disadvantage from a processing standpoint.

It is an object of this invention to provide aromatic biscyclopentadienone monomers that can be used in the preparation of thermally stable polymers having improved solubility parameters.

Other objects and advantages of the invention will become apparent to those skilled in the art upon consideration of the following disclosure.

DESCRIPTION OF THE INVENTION

In accordance with the present invention there is provided an aromatic biscyclopentadienone of the general formula

[Structure I: biscyclopentadienone with R, Ar, Ar' substituents]

wherein R is phenyl or p-bromophenyl;

Ar is p-methoxyphenyl, p-phenoxyphenyl, p-(phenylthio)phenyl, p-(phenoxyphenoxy)phenyl, p-[(phenoxyphenoxy)phenoxy]phenyl, p-cyanophenoxyphenyl, or p-hydroxyphenyl; and Ar' is phenylene, biphenylene, diphenylmethane, benzophenone, diphenyl sulfide, diphenyl ether, diphenyl sulfone, or biphenyl linkages.

The aromatic biscyclopentadienone monomer I is prepared by the reaction of an aromatic bis-benzil with a benzylketone. The reaction involved is represented by the following equation:

$$\text{Ar}-\underset{\text{II}}{\overset{\text{O}}{\text{C}}}-\overset{\text{O}}{\text{C}}-\text{Ar}'-\overset{\text{O}}{\text{C}}-\overset{\text{O}}{\text{C}}-\text{Ar} + 2\text{RCH}_2\overset{\text{O}}{\text{C}}\text{CH}_2\text{R} \underset{\text{III}}{\longrightarrow} \text{I}$$

wherein Ar, Ar' and R are as defined previously.

As shown by the above equation an aromatic bis-benzil is reacted with a 1,2-bisaromatic-2-propanone to form a biscyclopentadienone I. The compounds II and III are generally employed in a ratio of about 1:2, respectively, although the ketone III may be employed in excess, i.e., up to about 50% if desired. The reaction is carried out in the presence of an alkali metal hydroxide under reflux conditions in a suitable reaction medium. An alcohol, such as ethanol, can be conveniently used as the reaction medium. The amount of alkali metal hydroxide can vary within rather broad limits, but generally ranges from about 0.1 to 0.75 mole per mole of the aromatic bis-benzil. The reaction medium is usually maintained under reflux conditions for a period ranging from 15 minutes to 1 hour. The biscyclopentadienone product I may be recovered from the reaction mixture by conventional procedures, such as by filtration. It may, if desired, be further purified by chromatography.

The aromatic bis-benzils of Formula II are well known compounds that are described in the literature. Examples of such compounds include:

m-bis(p'-methoxyphenylglyoxylyl)benzene,
m-bis(p'-phenoxyphenylglyoxylyl)benzene,
m-bis[p'-(p''-phenoxy)phenoxyphenylglyoxylyl]benzene,
m-bis[p'-(p''-[p'''-phenoxy]phenoxy)phenoxyphenylglyoxylyl]benzene,
m-bis[p'-(p''-cyano)phenoxyphenylglyoxylyl]benzene, and
m-bis(p'-hydroxyphenylglyoxylyl)benzene.

The benzylketone III may be 1,3-bisphenyl-3-propanone or a halogenated derivative thereof, such as 1,3-bis(p-bromophenyl)-2-propanone.

The biscyclopentadienone monomers I of the present invention can be polymerized with acetylene-terminated comonomers to prepare polymers having the general formula

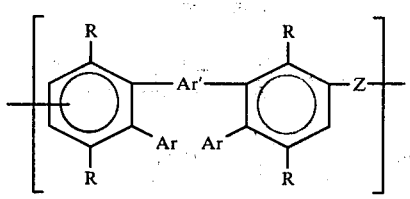

wherein Ar, Ar' and R are as defined previously, Z is a divalent heterocyclic radical and n is an integer equal to the number of repeating units. The polymer IV and the process for preparing same are more fully described in application Ser. No. 366,744, filed by us as coinventors, of even date herewith.

One of the diacetylenic heterocyclic monomers employed in making the polymer IV, as described in the aforesaid application Ser. No. 366,744, has the general formula

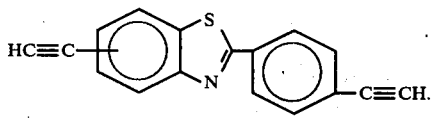

This compound is more fully described in application Ser. No. 356,576, filed by one of us as coinventor on Mar. 9, 1982.

The polymers IV are soluble in a variety of low-boiling, non-acidic solvents. Examples of suitable solvents include chloroform, benzene, toluene, 1,2,4-trichlorobenzene, and the like.

The following examples illustrate the invention.

EXAMPLE I

Preparation of 3,3'-(1,3-phenylene)bis(2,5-diphenyl-4-p-phenoxyphenylcyclopentadienone)

A stirred suspension of 10 g (19 mmol) of m-bis(p'-phenoxyphenylglyoxylyl)benzene and 8.4 g (40 mmol) of 1,3-diphenylacetone in 250 ml of 95% ethanol was heated to reflux. To this mixture was added 20 ml of 0.53N KOH in 2 portions over a period of 5 minutes. The reaction mixture changed color to purple immediately upon addition of the first portion of KOH. Heating was continued for 40 minutes, during which time a purple precipitate formed. The reaction mixture was cooled in ice, filtered and air dried. The crude production was purified by chromatography on a dry silica gel column using toluene as the eluent. 15.2 g recovered. (82.7% yield) m.p. 205°–206° C.

Analysis Calc'd for $C_{64}H_{42}O_4$: C, 87.85; H, 4.84; Found: C, 87.50; H, 5.10.

EXAMPLE II

Preparation of 3,3'-(1,3-phenylene)bis(2,5-diphenyl-4-p-thiophenoxyphenylcyclopentadienone A solution of 10 g (17.9 mmol) of m-bis(p'-thiophenoxyphenylglyoxylyl)benzene and 10.5 g (50 mmol) of 1,3-diphenylacetone in 225 ml of 95% ethanol was heated to reflux. To the reaction mixture was added 25 ml of 0.53N KOH. Upon addition of the KOH, the solution changed color to brown. Heating was continued for 30 minutes. The reaction mixture was allowed to cool to room temperature, then filtered and air dried, providing 16 g (98.8% yield) of crude product. This crude product was purified by column chromatography using dry silica gel and toluene as the eluent. The purified product melted at 246°–248° C.

Analysis Calc'd for $C_{64}H_{42}S_2O_2$: C, 84.73; H, 4.66; Found: C, 84.57; H, 4.42.

EXAMPLE III

Polymer Preparation

A mixture of 3.368 g (3.85 mmol) of 3,3'-(1,3-phenylene)bis-(2,5-diphenyl-4-p-phenoxyphenylcyclopentadienone) and 1.0 g (3.85 mmol) of 2-(3-ethynylphenyl)-5-ethynylbenzothiazole (m.p. 169° C.) was placed in a 20 ml polymerization tube with 7 ml of sym-tetrachloroethane. The contents of the tube were degassed by several freeze-thaw cycles at liquid nitrogen temperature, then sealed in vacuo. The sealed polymerization tube was placed in a Parr Bomb pressure reactor and heated to 225° C. for 42 hours. The tube was cooled to room temperature. After opening, 8 ml of chloroform was added to the viscous solution in the tube. The tube contents were poured into methanol to precipitate out the polymer, which was recovered by filtration, yielding 4.0 g (96% of theoretical). The polymer exhibited an intrinsic viscosity of 0.30 as determined in N,N-dimethylacetamide at 30° C.

Analysis Calc'd for $C_{79}H_{51}NSO_2$: C, 87.99; H, 4.77; Found: C, 87.70; H, 4.58.

Various modifications of the present invention can be made in view of the foregoing disclosure without departing from the spirit and scope of the invention.

We claim:

1. An aromatic biscyclopentadienone having the general formula

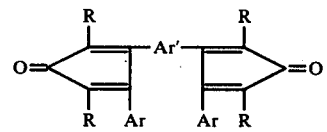

wherein Ar is a monovalent aromatic radical selected from the group consisting of

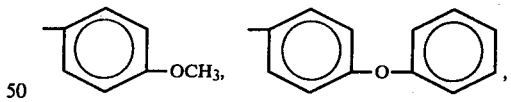

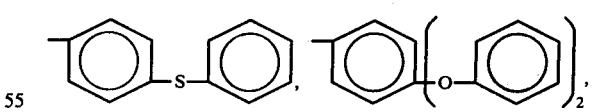

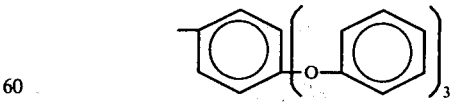

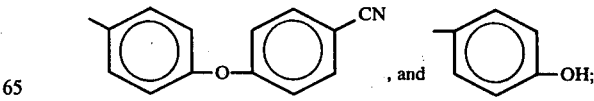

Ar' is a divalent aromatic radical selected from the group consisting of

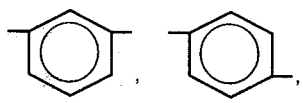
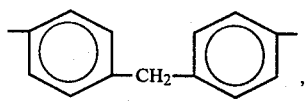
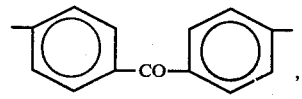
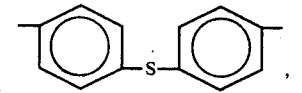
-continued
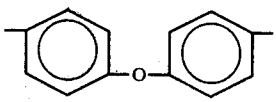
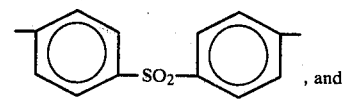, and
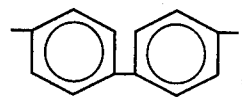
and R is a monovalent aromatic radical selected from the group consisting of
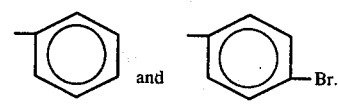
2. The compound of claim 1 wherein R is phenyl, Ar is p-phenoxyphenyl and Ar' is 1,3-phenylene.
3. The compound of claim 1 wherein R is phenyl, Ar is p-thiophenoxyphenyl and Ar' is 1,3-phenylene.
* * * * *